United States Patent [19]
Ware

[11] 4,314,562
[45] Feb. 9, 1982

[54] ENCLOSURE SYSTEM FOR BODY IMPLANTABLE ELECTRICAL SYSTEMS

[75] Inventor: Lyle A. Ware, Bloomington, Minn.

[73] Assignee: Medtronic, Inc., Minneapolis, Minn.

[21] Appl. No.: 114,714

[22] Filed: Jan. 23, 1980

Related U.S. Application Data

[63] Continuation-in-part of Ser. No. 7,307, Jan. 29, 1979, Pat. No. 4,243,042, which is a continuation of Ser. No. 793,638, May 4, 1977, abandoned.

[51] Int. Cl.³ .............................................. A61N 1/00
[52] U.S. Cl. ................................................. 128/419 P
[58] Field of Search ........ 128/419 P, 419 PG, 419 PS

[56] References Cited
U.S. PATENT DOCUMENTS

| | | | |
|---|---|---|---|
| 3,357,434 | 12/1967 | Abell | 128/419 P |
| 3,683,932 | 8/1972 | Cole | 128/419 PG |
| 3,842,842 | 10/1974 | Kenny et al. | 128/419 P |
| 3,949,937 | 3/1976 | King et al. | 128/419 P |
| 4,010,760 | 3/1977 | Kraska et al. | 128/419 P |

Primary Examiner—William E. Kamm
Attorney, Agent, or Firm—Schroeder, Siegfried, Ryan, Vidas, Steffey & Arrett

[57] ABSTRACT

An improved body implantable electrical stimulator assembly of the type having interconnected electrical components housed within a preformed enclosure. A cup is provided in which the components may be finally assembled, the cup being configured to fit within the enclosure. Preferably, the enclosure is formed of a plurality of members at least one of which has a main wall and a side wall joined at a radius. The cup is similarly formed of a main wall and a side wall, the main wall being generally coextensive with at least a major portion of the enclosure member main wall. The cup may engage the enclosure in a manner such that its movement within the enclosure is limited. Movement of the components within the cup may also be restrained. A cover for the cup may also be provided.

24 Claims, 18 Drawing Figures

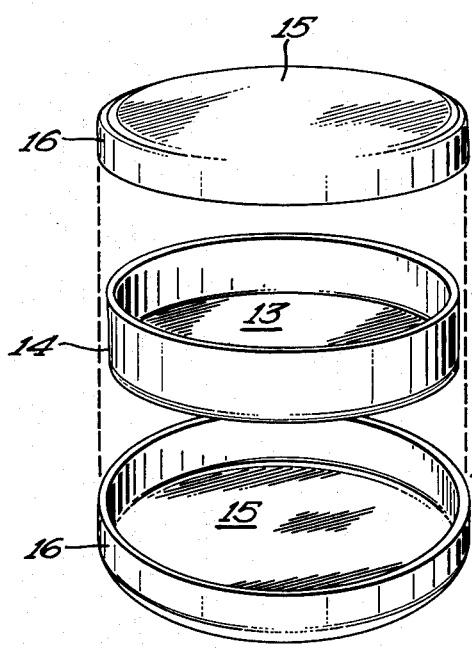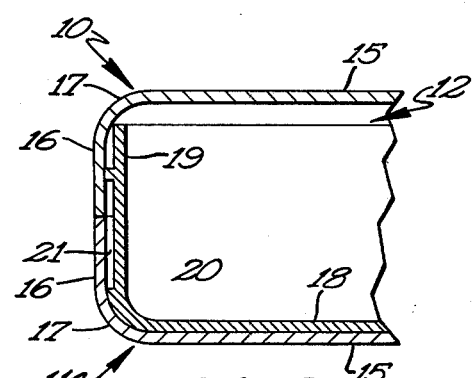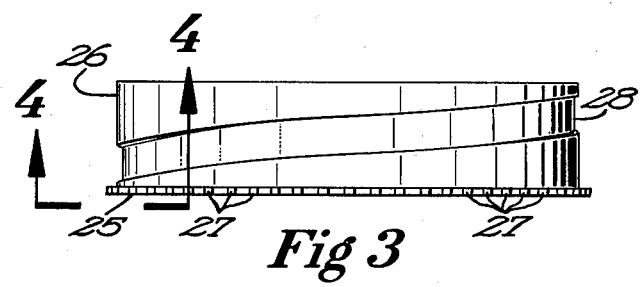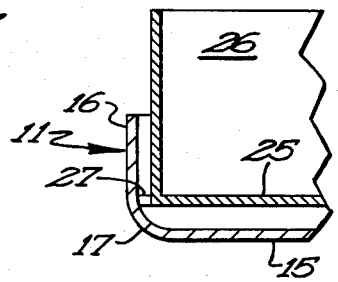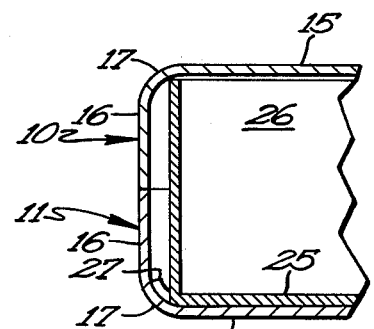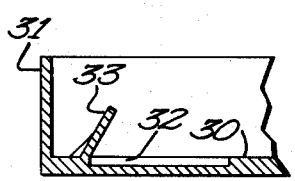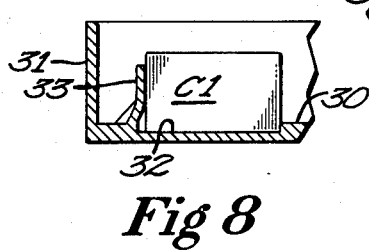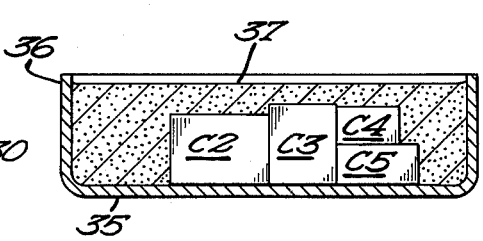

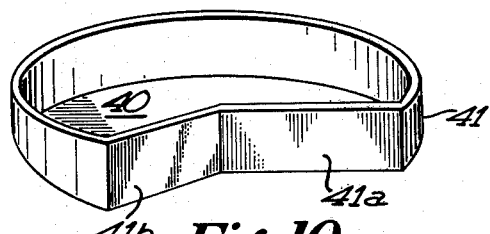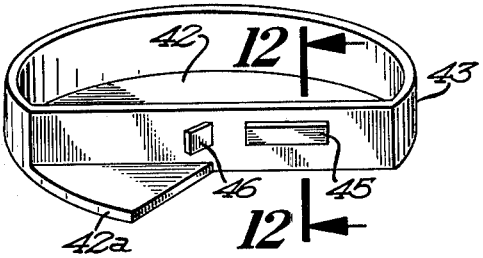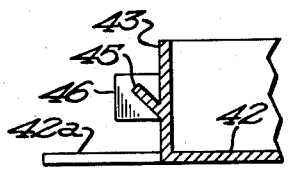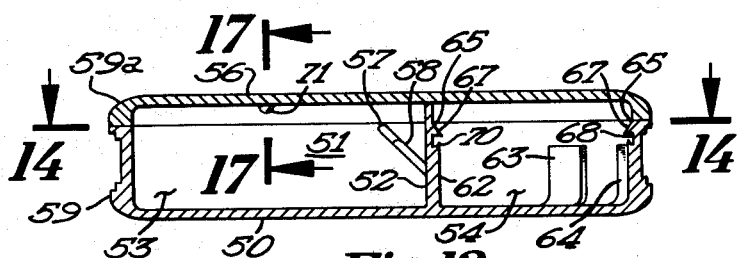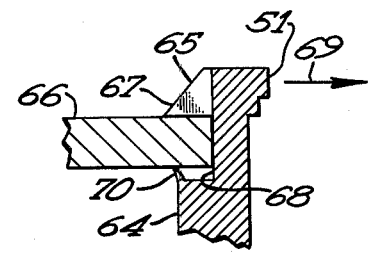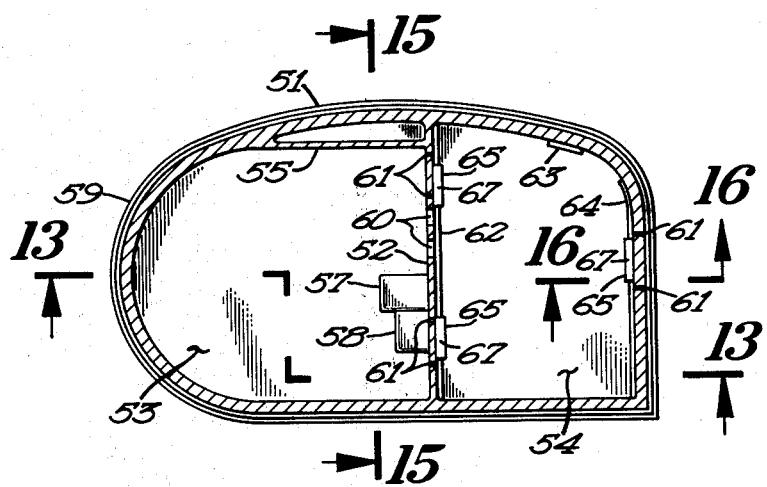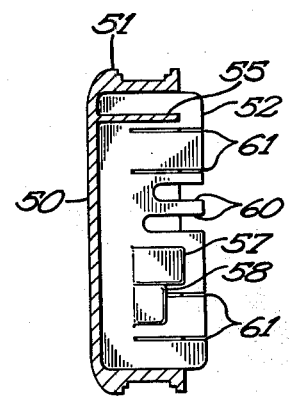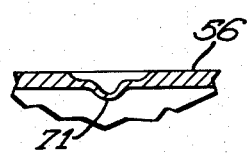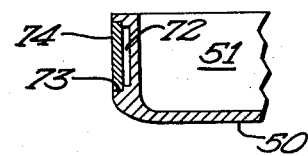

ENCLOSURE SYSTEM FOR BODY IMPLANTABLE ELECTRICAL SYSTEMS

DESCRIPTION cl BACKGROUND OF PRIOR ART

This is a continuation-in-part of application Ser. No. 7,307 filed Jan. 29, 1979, now U.S. Pat. No. 4,243,042 which is a continuation of application Ser. No. 793,638 filed May 4, 1977, now abandoned.

Body implantable electrical stimulators are well known to the prior art, the most common being the cardiac pacemaker. The electrical components forming such stimulators have been housed in a matrix of molded material which supports the components and shields them from the body environment. More recently, the electrical components forming the stimulator have been housed within a rigid enclosure formed of a plurality of preformed members which are typically welded together to complete the enclosure.

Some of the problems attending the use of a preformed rigid enclosure for a body implantable electrical stimulator are the need to electrically insulate the components from the enclosure, isolation of the components against shock and vibration, and securement of the components within the enclosure. These problems have been addressed by molding the assembled electrical components within a matrix of material to support the components relative to each other and provide an isolation between the components and the enclosure, with the molded matrix then being secured to the enclosure, as by an adhesive.

BRIEF SUMMARY OF THE INVENTION

The present invention provides a cup in which the components of a body implantable electrical stimulator may be assembled, the cup being configured to fit within a preformed electrical stimulator enclosure. The components are secured within the cup, and the cup may be provided with means for mechanically limiting its movement within the enclosure. Thus, the necessity of molding the assembled components is eliminated as is the need to secure the component mold within the enclosure. The components may be secured within the cup by an encapsulating material which substantially fills the cup, or by elements which engage one or more components to mechanically maintain them in position. In a preferred embodiment, the enclosure is formed of a plurality of members at least one of which has a main wall and a side wall joined at a radius. The cup is formed of a main wall and a side wall, the cup main wall being generally coextensive with at least a major portion of the enclosure member main wall with the cup side wall encircling the components. The cup may further be provided with means engaging the enclosure member radius to limit movement of the cup within the enclosure. The cup side wall may be provided with an antenna coil form when an antenna is required by the stimulator in question. In another preferred embodiment, the cup may be divided into compartments by a wall with the outer surface of the cup side wall being provided with a welding back-up ring. A cover may also be provided.

BRIEF DESCRIPTION OF THE DRAWINGS

FIG. 1 is an exploded view illustrating a two member preformed enclosure and the cup of the present invention.

FIG. 2 illustrates a cross-section of a preferred embodiment of the cup of the present invention and its cooperation with enclosure members of FIG. 1.

FIG. 3 illustrates another preferred embodiment of the cup of the present invention.

FIG. 4 is a view taken along the line 4—4 in FIG. 3.

FIGS. 5 and 6 illustrate the cooperation of the embodiment of FIGS. 3 and 4 with an enclosure member.

FIGS. 7 and 8 illustrate a preferred embodiment of the present invention.

FIG. 9 illustrates still another preferred embodiment of the present invention.

FIG. 10 illustrates an enclosure member to which the cup of the present invention may be adapted.

FIG. 11 illustrates an adaptation of the cup of the present invention to the enclosure member of FIG. 10.

FIG. 12 illustrates a cross-section taken along line 12—12 in FIG. 11.

FIG. 13 illustrates a cross-section of another preferred embodiment of the present invention taken along the line 13—13 in FIG. 14.

FIG. 14 illustrates a cross-section taken along the line 14—14 in FIG. 13.

FIG. 15 illustrates a cross-section taken along the line 15—15 in FIG. 14.

FIG. 16 is a cross-section taken along the line 16—16 in FIG. 14 that illustrates the function of a portion of the preferred embodiment of FIGS. 13-16.

FIG. 17 illustrates a cross-section taken along the line 17—17 in FIG. 13.

FIG. 18 illustrates the function of a portion of the preferred embodiment of FIGS. 13-16.

DETAILED DESCRIPTION OF THE DRAWINGS

FIG. 1 is an exploded view illustrating a concept of the present invention. An electrical stimulator enclosure is formed of first and second preformed members 10 and 11 which have generally circular main walls 15 and cylindrical side walls 16. The enclosure is formed by placing the side walls 16 together and joining them, as by welding. Enclosures of this type are known to the prior art, an example being that disclosed in copending application Ser. No. 659,650 filed Feb. 20, 1976, now U.S. Pat. No. 4,057,068 which is co-owned with the present application, and is incorporated herein by reference. As illustrated in FIG. 1, members 10 and 11 are identical. Within the context of the present invention, however, only one of the members 10 and 11 need have a main wall and a side wall. The members 10 and 11 may be any desired shape but, preferably, have a generally cylindrical side wall. Within the cylindrical side wall, provision may be made for electrical communication with components housed within the enclosure in a manner similar to that of the incorporated patent application, for example.

A cup 12 is illustrated in FIG. 1 having a main wall 13 and side wall 14, the cup being configured to fit within and substantially fill the enclosure formed by the members 10 and 11. The components forming the electrical stimulator may be assembled within the cup 12, the cup 12 then being placed within the member 11, the member 10 being placed over the cup and into engagement with the member 11, members 10 and 11 then being secured to each other, as by welding, for example. The cup 12, as illustrated in FIG. 1, greatly facilitates assembly of the components forming the electrical stimulator, and eliminates the otherwise required step of molding the assembled components. Additionally, the cup assists in the electrical insulation of the components from the enclosure and serves to isolate the components from shock and vibration. In preferred embodiments to be discussed below, the cup side wall may also be provided with a welding back-up ring or an antenna coil form when the use of an antenna is required.

In addition to assisting assembly of the stimulator components and insulating and isolating them from the enclosure, the cup which forms a portion of the present invention also serves to secure the components in position within the enclosure. The components are secured within the cup in a manner to be described more fully below. Additionally, the cup may substantially fill the enclosure or be provided with means for mechanically limiting its movement within the enclosure, thereby limiting movement of the components relative to the enclosure.

A preferred system for limiting the movement of the cup relative to the enclosure is illustrated in FIG. 2 which is a cross-section of an assembled enclosure of the type illustrated in FIG. 1, with a preferred cup embodiment positioned therein. As illustrated, members 10 and 11 each have a main wall 15 which is generally circular (see FIG. 1), and side wall 16, the main wall 15 and side wall 16 being joined to each other at a radius 17. The abutment of the side wall 16 of members 10 and 11 may be joined together as by welding, for example. Within the enclosure formed by the members 10 and 11, there is positioned a cup having a main wall 18 and a side wall 19. The cup is provided with a radius 20 at the outside junction of the main wall 18 and side wall 19, which is in substantial conformity with the radius 17 of the member 11. When urged into position, the radius 20 engages the radius 17 to mechanically prevent movement of the cup within the enclosure formed by the members 10 and 11 and, through friction, restricts rotation of the cup relative to the enclosure. Radius 20 is urged against the radius 17 by a force imparted to the cup, or its contents, by the member 10 when the side walls 16 are in abutment and is maintained in that position for so long as the enclosure remains closed. Preferably, the cup is made of a resilient or flexible material capable of conforming the radius 20 to the radius 17 under the influence of the force imparted to the cup via the member 10, while resisting deformation under that force which might relieve the engagement between the radius 20 and the radius 17. Polypropylene has been found to be a suitable material for the embodiment illustrated in FIG. 2, as well as the other embodiments illustrated herein. Other materials having the required properties may also be used, nylon, for example. The outer surface of the side wall 19 may be provided with a recess 21 above the radius 20 and running around its periphery to act as an antenna coil form. That is, an antenna may be wound or otherwise constructed within the recess 21 when the presence of an antenna is necessary to the operation of the electrical stimulator in question.

Referring now to FIG. 3, there is illustrated a side view of another preferred embodiment of the cup forming a part of the present invention. The cup of FIG. 3 has a main wall 25 and a side wall 26. Extending from the junction of the main wall 25 and side wall 26 are a plurality of finger-like members 27 (see FIG. 4) which function in a manner similar to the radius 20 in the embodiment of FIG. 2 to limit movement of the cup within the enclosure. The outer surface of the side wall 26 may be provided with a recess 28 to function as an antenna coil form when appropriate. The recess 28 may be equidistant from the main wall 25. As illustrated, however, the recess 28 is skewed relative to the main wall 25. That is, a plane through the recess 28 is skewed relative to the plane of the main wall 25. In this manner, an antenna within the recess 28 will be closer to the main wall of enclosure member 10 in one location and closer to the main wall of enclosure member 11 in another location so as to increase its sensitivity beyond that which might otherwise be possible if the recess 28 were equidistant in all places from the main wall 25 and, thus, the main walls of the members 10 and 11. Additionally, the skewing of the recess 28 provides a larger antenna coil diameter than would be the case if the recess 28 were equidistant from the main wall 25.

Referring now to FIGS. 5 and 6, the cooperation of the finger members 27 with the radius 17 of one of the enclosure members is illustrated. The cup of FIG. 3 is positioned within the enclosure member 11, the members 27 engage the inner surface of the radius 17, and maintain the main wall 25 of the cup spaced from the main wall 15 of the enclosure member 11. A force is imparted to the cup, or its contents, by the enclosure member 10 when the side wall 16 of the enclosure members 10 and 11 are in abutment. This force causes the members 27 to deform and resiliently engage the inner surface of the radius 17 (see FIG. 6) thereby limiting both lateral and rotational movement of the cup within the enclosure. The resilient nature of the cup material causes the members 27 to continually engage the inner surface of the radius 17 and maintain the motion limitation provided thereby.

To this point, there has been described preferred embodiments of a cup member in which the electrical components that embody the implantable stimulator may be assembled and which cooperates with the members forming an enclosure for the stimulator to limit movement of the cup member within the enclosure. FIGS. 7 and 8 illustrate a preferred embodiment for restraining the movement of at least some of the components forming the electrical stimulator. FIGS. 7 and 8 show a partial cross-section of a cup member having a main wall 30 and a side wall 31. The junction of the main wall 30 and side wall 31 may be provided with a radius 20 or members 27 as described above with reference to FIGS. 2-6. The inner surface of the main wall 30 is provided with a recess 32 of a size which will accept one of the stimulator electrical components. Extending from the main wall 30 and over the recess 32 is a spring tab 33 which may be unitary with the main wall 30. An electrical component C1 (see FIG. 8) may be inserted within the recess by engaging it against the spring tab 33 to deflect or push it out of blocking relation relative to the recess 32 and putting the component C1 within the recess 32. Spring tab 33 will then engage the component C1 and urge it against the recess wall in a manner which will maintain the component C1 within the recess. Electrical components of the type employed within a body implantable electrical stimulator are manufactured to nominal dimensions within a stated tolerance range. The recess 32 is made large enough to accept all components within the given tolerance range and the spring tab 33 will engage all components within the tolerance range to urge them against the wall of the recess 32. Therefore, not only does the cooperation between the recess 32 and spring tab 33 maintain a component in position within the cup, the cooperation of those elements accommodates parts of varying dimensions within a known tolerance range (tolerance accumulation). One or more recesses 32 and spring tabs 33 may be provided within the main wall 30 to accommodate one or more major components of the stimulator to secure and maintain them in position within the cup, the cup being limited in its movement within the enclosure formed by members 10 and 11, as stated above. Therefore, components secured within the cup as illustrated with reference to component C1 are secured against movement within the enclosure as well.

Referring now to FIG. 9, there is shown an alternative embodiment for securing the assembled electrical components within a cup. The cup is formed of a main wall 35 and a side wall 36 whose junction may be provided with a radius 20 or finger members 27 as described above with reference to FIGS. 2–6. Components C2–C5 are assembled within the cup and the cup is substantially filled with an encapsulating material 37 which forms a matrix surrounding the components C2–C5 to hold them in position relative to each other and secure them within the cup. The cup is then positioned within the enclosure formed by members 10 and 11 with the components C2–C5 being maintained in position relative to the cup and the enclosure. The encapsulating material 37 may be silicone rubber or another similar material suitable for use in a body implantable device.

As discussed above, the incorporated patent makes provision for electrical communication with the enclosed electrical stimulator. In the incorporated patent, this is accomplished through the use of a recess within one of the side walls of the enclosure member. A similar but alternative enclosure member is illustrated in FIG. 10 which has a main wall 40 and a side wall 41 joined at a radius such as that illustrated in FIGS. 2, 5 and 6. The side wall 41 is generally cylindrical, having platforms 41a and 41b through which electrical communication may be made. The enclosure may be completed with a plate welded to the end of the side wall 41 or with a complimentary member having a side wall corresponding to the side wall 41 of the same or a different height than the side wall 41. A cup for use in an enclosure formed at least in part by a member such as that illustrated in FIG. 10 is illustrated in FIG. 11. The cup of FIG. 11 includes a main wall 42 which is generally coextensive with at least a major portion of the main wall 40 of the member of FIG. 10. A side wall 43 extends from the main wall 42 and encircles an area in which the electrical components are to be assembled. The main wall contains a portion 42a which extends beyond that area encircled by the side wall 43. The junction between the main wall 42 and side wall 43 may be provided with a radius 20 or finger members 27 as illustrated in FIGS. 2–6. Preferably, the finger members 27 of FIGS. 3–6 extend from the junction of the main wall 42 and side wall 43 as well as from the main wall portion 42a to engage the radius between the main wall 40 and side wall 41 of the enclosure member of FIG. 10 as described above. Additionally spring tabs 45 and 46 may be provided to engage the platforms 41a and 41b, respectively, the spring tab 45 urging the cup member away from the platform 41a while the spring tab 46 engages the platform 41b to assist in preventing rotation of the cup member within the enclosure member. The spring tab 46 may be used in combination with the main wall portion 42a, or as an alternative to it for the purpose of preventing rotation. The spring tabs 45 and 46 facilitate and enhance the engagement between the radius 20 or finger members 27 with the inner surface of radius 17, as discussed above with reference to FIGS. 2–6. The major functions of the present invention, however, may be accomplished through the use of the radius 20 and/or finger members 27 without the use of the spring tabs. Within the context of the incorporated patent, the spring tab 46 may be angled to cooperate with the reverse side of platform 31 illustrated in FIGS. 5–7 of the incorporated patent for the purpose essentially as described herein, with or without the main wall portion 42a.

Referring now to FIG. 13, there is illustrated, in cross-section taken along the line 13—13 in FIG. 14, another preferred embodiment of the present invention directed particularly to restraint of the components within the cup. FIG. 14 is a cross-section taken along the line 14—14 in FIG. 13 and, together with FIG. 13, illustrates that the cup is formed by a main wall 50 and a side wall 51. An inner wall 52 divides the cup into two compartments 53 and 54. Compartment 53 is designed to house a power supply while compartment 54 is intended to house the electrical signal generating components. A second inner wall 55 is provided in compartment 53 to configure that compartment for a particular battery configuration and, beyond that function, forms no part of the present invention. A cover 56, coextensive with the cup, may be provided and will be discussed more fully below.

Compartment 53 is provided with spring tabs 57 and 58 which function in a manner similar to the spring tab 33 of FIGS. 7 and 8. As noted above, compartment 53 is adapted to accept a power source of a particular configuration. That configuration is generally rectangular having one rounded end. Thus, side wall 51 is provided with a rounded portion as at 59 to accommodate the rounded end of the power source. In addition, the dimension between the rounded portion of the power source and the power source end that will lie most closely to the inner wall 52 varies dependent on the particular battery model being employed. Thus, two tabs 57 and 58 are provided, the longer tab 57 for the shorter power source and the shorter tab 58 for the longer power source. The spring tab 57 or 58 which will not be employed may be severed as by cutting with a knife edge, for example. In any event, the spring tab 57 or 58 which is to be employed is engaged by the non-rounded edge of the power source and deflected or pushed back toward the inner wall 52 such that the power source rounded end can be positioned within the compartment 53. The spring tab then urges the power source against rounded portion 59 of side wall 51. The upper portion 60 of curved portion 59 of side wall 51 (see FIG. 13) is configured so as to project up and over a power source within the compartment 53 to assist in maintaining that power source within that compartment. Of course, any other configuration adapted to any particular power source configuration may be employed without departing from the scope of the present invention.

A view of inner wall 52 is illustrated in FIG. 15 which is a cross-section taken along the line 15—15 in FIG. 14. FIG. 15 illustrates the spring tabs 57 and 58 carried by the inner wall 52 as well as gaps 60 within the wall. Gaps 60 allow electrical communication between the compartments 53 and 54 as by the extension of wires therethrough. Slots 61 are also provided within inner wall 52 and will be discussed more fully below.

Compartment 54 is adapted to receive and contain the electrical elements that form the stimulation signal. The electrical elements are carried by or contained on a substrate and, within the context of the present invention, may take any form within the constraint that a substrate is employed. Compartment 54 is provided with ledges 62–64 which may be unitary with side wall 51 and inner wall 52 and which are adapted to support the electrical element bearing substrate. Also carried by side wall 51 and inner wall 52 are members 65 which cooperate with the ledges 62–64 to maintain the substrate in position within the compartment 54. These members are illustrated in FIG. 16, which is a cross-section taken along the line 16—16 in FIG. 14, together with a substrate 66 in the position in which it is to be maintained. Member 65 includes a bearing surface 67 and is spaced from the ledge 64 to form a groove or dado 68 within the inner surface of side wall 51. Members 65 are positioned intermediate adjacent slots 61 such that they may deflect without distortion of the side wall 51 or inner wall 52 of which they are a part. For example, a force exerted on bearing surface 67 will result in a deflection of the side wall 51 intermediate the slots 61 in the direction of the arrow 69. Such a deflection is caused on insertion of the substrate 66 by engagement of the substrate 66 with the bearing surface 67. A projection 70 may be provided within the groove or dado 68 for tolerance accumulation to accommodate different thicknesses from one substrate 66 to another.

Referring now to FIG. 13, and particularly the cover 56, there is provided within the compartment 53, on the under side of cover 56, a bubble 71. Bubble 71 is adapted to engage a component within the compartment 53 to assist in maintaining that component within the desired position within compartment 53. One or more bubbles 71 may be employed and they may be positioned either within the cover 56 or within the main wall 50 of the cup. As illustrated in FIG. 17, the bubble 71 may be integral with the cover 56 or wall 50, as by molding it therein. The primary constraint on bubble 71 is that it be resilient to accomplish its intended purpose.

Referring now to FIG. 18, there is illustrated an alternative embodiment for the outer surface of side wall 51, and any of the side walls of the other embodiments illustrated herein. The outer surface is provided with a first recess 72 and a second recess 73 which is shallower and wider than the recess 72 but overlies recess 72. A metal band may be positioned within the recess 73 with recess 72 providing an air gap between the central portion of the band 74 and the cup side wall 51. The band 74 should be positioned behind the abutment of the two members forming the enclosure in which the cup is to be housed so as to provide a welding back-up ring at the welding location. The air gap formed by recess 72 provides insulation between the welding back-up ring formed by band 74 and the cup side wall 51 at the location of the weld. In this manner, a greater security against a burn-through of the side wall 51 of the cup is provided.

Obviously, many modifications and variations of the present invention are possible in light of the above teachings. For example, the configuration of the main wall and side wall of the cup member described herein may be configured to be accommodated within any enclosure formed of two or more members whether generally cylindrical or otherwise. The cup member need not totally fill the enclosure, but should preferably substantially fill the enclosure to minimize wasted space within the enclosure and maximize the contact between the enclosure member radius and the cup member radius engaging means. In addition, the use of spring tabs such as 45 and 46 may or may not be necessary within the context of a particular enclosure configuration, that decision being within the skill of one ordinarily skilled in the art having reference to the teachings herein. Accordingly, within the scope of the appended claims, the invention may be practiced other than as specifically described.

I claim:

1. In a body implantable stimulator of the type having interconnected components housed within a preformed enclosure, the improvement which comprises insulating and isolating cup means formed of a resilient, non-conductive material and configured to accept said components and substantially fill said enclosure, said cup means further comprising resilient means engaging at least one component for maintaining said component in a preselected position within said cup means.

2. The body implantable stimulator of claim 1 wherein said resilient means comprises tolerance accumulation means.

3. The body implantable stimulator of claim 1 wherein said cup means comprises at least one compartment, said resilient means comprising means for deflecting to allow insertion of said component within said compartment.

4. The body implantable stimulator of claim 3 wherein said resilient means comprises tab means for engaging a component within said compartment and urging it against an abutment means.

5. The body implantable stimulator of claim 4 wherein said abutment means comprises at least a portion of a wall forming said compartment.

6. The body implantable stimulator of claim 5 wherein said compartment wall comprises means for extending partially over a component within said compartment.

7. The body implantable stimulator of claim 3 wherein said component comprises substrate means, said resilient means comprising dado means for accepting said substrate means.

8. The body implantable stimulator of claim 7 wherein said resilient means comprises a plurality of dado means.

9. The body implantable stimulator of claim 8 wherein said dado means are in wall means of said compartment, said wall means being slotted adjacent said dado means.

10. The body implantable stimulator of claim 9 wherein said dado means are provided with tolerance accumulation means.

11. The body implantable stimulator of claim 10 wherein said tolerance accumulation means comprise projecting means within said dado means.

12. The body implantable stimulator of claim 3 wherein said cup means comprises two compartments each having resilient means.

13. The body implantable stimulator of claim 12 wherein the resilient means of one compartment comprises tab means for urging a component within said one compartment against an abutment means.

14. The body implantable stimulator of claim 13 wherein the resilient means of the other compartment comprise dado means within wall means of said compartment.

15. The body implantable stimulator of claim 14 wherein said dado means are provided with tolerance accumulation means.

16. The body implantable stimulator of claim 15 wherein said tolerance accumulation means comprise projecting means within said dado means.

17. The body implantable stimulator of claim 16 wherein said resilient means comprises a plurality of dado means.

18. The body implantable stimulator of claim 17 wherein said wall means are slotted adjacent said dado means.

19. The body implantable stimulator of claim 16 wherein said wall means are slotted adjacent said dado means.

20. The body implantable stimulator of claim 19 wherein said abutment means comprises at least a portion of a wall forming said one compartment.

21. The body implantable stimulator of claim 20 further comprising cover means generally coextensive with said cup means, at least one of said cover means and cup means having resilient bubble means for engaging and maintaining at least one component in a desired position within said cup means.

22. The body implantable stimulator of claim 21 wherein the outer surface of the cup means side wall is provided with a first recess around its periphery and a second recess wider and shallower than the first recess and overlying the first recess, and further comprising a welding back-up ring within said second recess.

23. The body implantable stimulator of claim 1 further comprising cover means generally coextensive with said cup means, at least one of said cover means and cup means having resilient bubble means for engaging and maintaining at least one component in a desired position within said cup means.

24. The body implantable stimulator of claim 1 wherein said enclosure is joined by welding and the outer surface of the cup means side wall is provided with a first recess around its periphery and a second recess wider and shallower than the first recess and overlying the first recess, and further comprising a welding back-up ring within said second recess.

* * * * *